United States Patent [19]

Gebauer et al.

[11] Patent Number: 4,704,477

[45] Date of Patent: Nov. 3, 1987

[54] TRIMETHYLCYCLOHEXENE DERIVATIVES, THEIR PREPARATION AND USE AS PERFUME SUBSTANCES

[75] Inventors: Helmut Gebauer, Munich; Hans Mehlin, Neuried; Marlies Regiert, Munich, all of Fed. Rep. of Germany

[73] Assignee: Consortium fur Elektrochemische Industrie GmbH, Munich, Fed. Rep. of Germany

[21] Appl. No.: 837,218

[22] Filed: Mar. 7, 1986

[30] Foreign Application Priority Data

Apr. 23, 1985 [DE] Fed. Rep. of Germany ....... 3514665

[51] Int. Cl.$^4$ ............................................. C07C 49/21
[52] U.S. Cl. ................. 568/377; 568/826; 568/349; 252/522 R; 560/128; 512/22; 512/24
[58] Field of Search ............... 568/349, 377, 826, 827; 560/128; 252/522 R

[56] References Cited

U.S. PATENT DOCUMENTS

| | | | |
|---|---|---|---|
| 2,794,812 | 6/1957 | Phillips et al. | 560/128 |
| 3,067,244 | 12/1962 | Robinson et al. | 568/349 |
| 4,250,342 | 2/1981 | Sprecker et al. | 568/826 |
| 4,369,328 | 1/1983 | Schulte-Clte et al. | 560/128 |
| 4,375,001 | 2/1983 | Schenk et al. | 560/128 |
| 4,528,020 | 6/1985 | Sprecker et al. | 568/377 |

FOREIGN PATENT DOCUMENTS 7404606 10/1974 Netherlands ................. 568/377

OTHER PUBLICATIONS

Morrison et al., "Organic Chemistry", p. 666 (1966).
Fieser et al., "Reagents for Organic Synthesis", vol. 1, pp 597–598, 1050–1051, 1058–1064 and 1158–1160 (1967).
Chadroff et al., Chem. Abst., vol. 91, #216694f (1979).

*Primary Examiner*—James H. Reamer
*Attorney, Agent, or Firm*—Collard, Roe & Galgano

[57] ABSTRACT

Compounds of the general formula

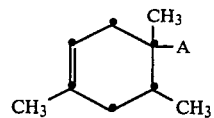

wherein
A is the

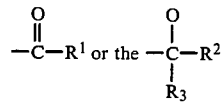

group and in which
$R^1$ stands for hydrogen, methyl, ethyl, n-propyl, isopropyl, methoxy, ethoxy, n-propoxy and isopropoxy and $R^2$ and $R^3$ are hydrogen, methyl and ethyl. The compounds are used as perfume substances.

5 Claims, No Drawings

TRIMETHYLCYCLOHEXENE DERIVATIVES, THEIR PREPARATION AND USE AS PERFUME SUBSTANCES

The invention relates to new compounds from the 1,4,6-trimethylcyclohex-3-ene derivatives group, a process for their preparation, and a perfume containing the same.

According to S. Arcander, "Perfumes and Flavour Chemicals" (1969), 3,5,6-trimethylcyclohex-3-ene-1-carbaldehyde and 2,4,6-trimethylcyclohex-3-ene-1-carbaldehyde are known in the art. The fragrance picture of these perfume substances mentioned is defined by sweet, floral notes.

It was then found that a selection of 1,4,6-trimethylcyclohex-3-enes that have, according to the invention, a quarternary carbon atom in the 1 position are classed in the fragrance spectrum in a region entirely different from that of the known trimethylcyclohexene derivatives mentioned above, namely in the region of the spicy and woodsy notes. It must especially be emphasized that some representatives of the compounds according to the invention reproduce the intrinsic olfactory aspects of natural patchouli oil.

Accordingly, it is an object of the invention to provide new compounds from the 1,4,6-trimethylcyclohex-3-ene derivatives group which are especially useful as fragrant substances and a process for their manufacture.

More particularly, it is an object of the invention to provide synthetic fragrant substances from the 1,4,6-trimethylcyclohex-3-ene derivatives group having a fragrance picture within the range of woody and spicy notes.

This and related objects of the invention are achieved by providing compounds of the general formula

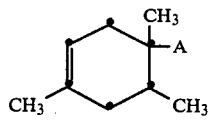

in which A is the

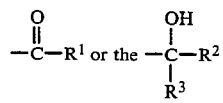

group and in which $R^1$ stands for hydrogen, methyl, ethyl, n-propyl, isopropyl, methoxy, ethoxy, n-propoxy and isopropoxy, and $R^2$ and $R^3$ are either hydrogen, methyl and ethyl.

Examples of compounds according to the invention are:
1,4,6-trimethylcyclohex-3-ene-1-carbaldehyde
1,4,6-trimethylcyclohex-3-ene-1-carboxylic acid methyl ester
1,4,6-trimethylcyclohex-3-ene-1-carboxylic acid ethyl ester
1,4,6-trimethylcyclohex-3-ene-1-carboxylic acid propyl ester
1,4,6-trimethylcyclohex-3-ene-1-carboxylic acid isopropyl ester
(1,4,6-trimethylcyclohex-3-en-1-yl)-methanol
1-(1,4,6-trimethylcyclohex-3-en-1-yl)-ethan-1-ol
1-(1,4,6-trimethylcyclohex-3-en-1-yl)-propan-1-ol
2-(1,4,6-trimethylcyclohex-3-en-1-yl)-propan-2-ol
2-(1,4,6-trimethylcyclohex-3-en-1-yl)-butan-2-ol
3-(1,4,6-trimethylcyclohex-3-en-1-yl)-pentan-3-ol
1-(1,4,6-trimethylcyclohex-3-en-1-yl)-ethan-1-one
1-(1,4,6-trimethylcyclohex-3-en-1-yl)-propan-1-one
1-(1,4,6-trimethylcyclohex-3-en-1-yl)-butan-1-one
1-(1,4,6-trimethylcyclohex-3-en-1-yl)-3-methylpropan-1-one.

The 1,4,6-trimethylcyclohex-3-ene-1-carbaldehyde according to the invention and the analogous ketones according to the invention are directly accessible by means of 1,4-cycloaddition of isoprene with tiglic aldehyde or with the corresponding 2-propenylalkyl ketones. The carbaldehyde according to the invention and the analogous ketones are directly accessible by 1,4-cycloaddition of tiglic aldehyde or the corresponding 2-propenylalkyl ketones with isoprene.

The primary and secondary alcohols according to the invention are obtained in a well-known manner by reduction of the aldehyde or by reduction of the corresponding ketones. Examples of suitable reducing agents are complex hydrides such as sodium borohydride, lithium aluminum hydride or aluminum isopropylate (Meerwein-Ponndorf reduction). The tertiary alcohols according to the invention are obtainable, for example, from the corresponding ketones in a well-known manner by reaction with Grignard compounds such as methyl- and ethylmagnesium halide.

The esters according to the invention are accessible by oxidation of the carbaldehyde to the acid (e.g. with chromosulfuric acid as the oxidizing agent) and subsequent esterification of the acid, if necessary via the carboxylic acid chloride intermediate step.

The preferred process for the preparation of the compounds according to the invention is characterized in that
(a) isoprene and a dienophile of the formula

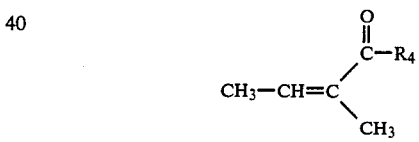

in which $R_4$ is hydrogen or an alkyl group with 1–3 carbon atoms are subjected to a 1,4-cycloaddition, and
(b) if necessary the resulting reaction product is converted
 (b1) by means of sodium borohydride, lithium aluminum hydride or aluminum isopropylate into the primary or secondary alcohol,
 (b2) by means of alkylmagnesium halide into the tertiary alcohol, or
 (b3) by oxidation to the acid and subsequent esterification to the ester.

Examples of dienophiles are tiglic aldehyde, 3-methylpent-3-en-2-one, 4-methylhex-4-en-3-one, 2,4-dimethylhex-4-en-3-one and 5-methylhept-5-en-4-one.

Within the scope of the invention, 1,4-cycloaddition (also known as the Diels-Alder reaction is understood to refer to the addition of a compound with 2 conjugated carbon double bonds onto an olefin whose carbon double bond is conjugated with a carbonyl group, with formation of a cyclohexene derivative. The remaining carbon double bond is thereby formed at that site which originally formed the connecting link between the conjugated double bonds of the diolefin. The isoprene (2-methylbuta-1,3-diene) and dienophile are advisably used in a molar ratio of 0.9–1.3 to 1, especially 1.01–1.3 to 1.

The reaction temperatures are primarily from 15° to 130° C. The reaction can be carried out both with and without a catalyst. When working without a catalyst a temperature range of 80° to 130° C. is preferred. In this case the reactions are advisably carried out in pressure apparatuses at 5 to 20 bar absolute. Thus, along with the 1,4,6-trimethylcyclohexene derivatives, the analogous 1,3,6-trimethylcyclohexene derivatives are also formed to a lesser extent. If desired, they can be separated by well-known methods, for example by chromatography.

In the presence of Lewis acids the formation of 1,3,6-trimethylcyclohexene species is largely suppressed. Moreover a catalytic effect is achieved that permits carrying out the 1,4-cycloaddition even at the ambient atmospheric pressure and at temperatures of 15° to 80° C. The Lewis acids are preferably added in amounts of 0.1 to 10 mole %, depending on the amount of dienophile to be reacted. Examples of Lewis acids to be used as catalysts according to the invention are aluminum chloride, zinc chloride, iron(III) chloride and others.

By way of example, the process is carried out in such a way that the dienophile and Lewis acid are put in first and the isoprene added in uniform amounts. The reaction temperatures in this case are advisably about 15° to 40° C. initially and are gradually raised to 60° to 80° C. by the end of the reaction. The reaction proceeds exothermally. Control of the reaction can be regulated, for example, via the isoprene dosage rate. In an additional process variant, the catalyst is put in an inert solvent such as e.g. dibutyl ether and a mixture of the isoprene, and dienophile reactants are added dropwise.

The compounds according to the invention are used as perfume substances or as ingredients of mixtures of perfume substances. They can be used alone or in admixture, and especially also in a mixture with the analogous 1,3,6-trimethylcyclohex-3-ene derivatives. The 1,3,6-trimethylcyclohexenes mentioned give off a fragrance picture very similar to that of the 1,4,6-cyclohex-3-ene derivatives.

The perfume substances according to the invention are classified within the range of woodsy and spicy notes. Along with fresh herbal fragrance notes, spicy floral to earthy woodsy fragrance notes, sometimes even distinct notes reminiscent of ginger, calamus and sage, are prominent. Without exception, they show high scent intensity.

The principal fragrance aspects of natural patchouli oil, which is available only in limited quantity and often of very variable quality, are prominent particularly with 1-(1,4,6-trimethylcyclohex-3-en-1-yl)ethan-1-ol, 1-(1,4,6-trimethylcyclohex-3-en-1-yl)propan-1-one, (1,4,6-trimethylcyclohex-3-en-1-yl)methanol and especially markedly with 1-(1,4,6-trimethylcyclohex-3-en-1-yl)-1-methylethan-1-ol and 1-(1,4,6-trimethylcyclohex-3-en-1-yl)-1-methylpropan-1-ol. The fragrance-determining ingredients of natural patchouli oil are the tricyclic sesquiterpene alcohol patchoulol and the related norpatchoulenol, for which as yet no economically practical syntheses are known. The previously-mentioned compounds now available according to the invention provide for perfume substances that are accessible entirely by synthetic means, and which can replace natural patchouli oil in fragrance compositions.

The invention will now be more fully described by the following examples, which are given by way of explanation and not by way of limitation.

EXAMPLE 1

Preparation of 1-(1,4,6-trimethylcyclohex-3-en-1-yl)ethan-1-one

Two moles (196 g) 3-methylpent-3-en-2-one and 0.1 moles (13.3 g) anhydrous aluminum chloride were put in a 1-liter 4-necked flask with a stirrer, reflux condenser, dropping funnel and internal thermometer. 3 moles (300 ml) isoprene were added dosewise to this mixture in such a way that the temperature of the reaction mixture rose to 80° C. Finally it was cooled, 100 ml 5% by wt. hydrochloric acid was added, and extraction was carried out. Then the organic phase was separated off and without further purification subjected to fractional distillation via a packed column 60 cm high. The yield of desired end product was 265 g, corresponding to 80% of the theoretical amount.

Boiling point: 93° C. at 16 mbar.

Odor: fresh-minty, green herbal, sweet balsamic, reminiscent of rosemary and sage.

EXAMPLE 2

Preparation of 1-(1,4,6-trimethylcyclohex-3-en-1-yl)ethanol

A solution of 0.33 moles (68 g) aluminum isopropylate in 600 ml isopropanol was heated to boiling in a 1-liter 3-necked flask with a magnetic stirrer, packed column, dropping funnel and thermometer. Within two hours 1 mole (166 g) 1-(1,4,6-trimethylcyclohex-3-en-1-yl)ethan-1-one (as per Example 1) was added dropwise to the boiling solution, and at the same time the isopropanol/acetone mixture formed was distilled off. After 10 hours the reaction was ended (after no more acetone could be detected in the distillate). Thereupon isopropanol still remaining was drawn off, and 175 ml 20% by weight hydrochloric acid was added to the residue after cooling. Extraction was carried out and the organic phase was washed free of acid. After fractional distillation 151 g of the desired end product was obtained, corresponding to 90% of the theoretical amount.

Boiling point: 65° C. at 0.2 mbar.

Odor: dry, earthy-woodsy-spicy, reminiscent of straw and calamus.

EXAMPLE 3

Preparation of 2-(1,4,6-trimethylcyclohex-3-en-1-yl)propan-2-ol (a) 0.5 moles (12 g) magnesium powder was placed in a 500-ml 4-necked flask with a magnetic stirrer, reflux condenser, dropping funnel, internal thermometer and gas inlet tube, and covered with a layer of 20 ml dry tetrahydrofuran and 1 ml ethyl bromide. After the startup of the reaction (gray coloration and heat change) another 110 ml tetrahydrofuran was added dropwise at 50° to 60° C. within an hour. At the same time methyl chloride was introduced into the admixture until all of the magnesium was reacted.

(b) 0.4 moles (66.4 g) 1-(1,4,6-trimethylcyclohex-3-en-1-yl)-ethan-1-one (as per Example 1) was then added dosewise at 70° C. to the reaction mixture according to (a). Then stirring was continued for another hour at 70° C. The reaction mixture was then cooled, poured on 300 g ice, and the precipitated magnesium salt was dissolved with 30 ml glacial acetic acid. Finally the phases were separated, the organic phase neutralized with sodium bicarbonate solution, the solvent drawn off and the residue subjected to fractional distillation. 30 g of the desired end product were obtained, corresponding to 40% of the theoretical amount.

Boiling range: 65°–67° C. at 0.2 mbar.

Odor: strongly herbal, woodsy, spicy, delicate-earth-balsamic, brillant marked patchouli.

EXAMPLE 4

Preparation of 1-(1,4,6-trimethylcyclohex-3-en-1-yl)propan-1-one 0.025 moles (3.3 g) anhydrous aluminum chloride were dissolved with vigorous stirring in 1 mole (112 g) 4-methylhex-4-en-3-one in a 250-ml 3-necked flask with a magnetic stirrer, high-power condenser, dropping funnel and internal thermometer. At 40° C. 1.5 moles (150 ml) isoprene was added dropwise to this solution. After this addition ended, the reaction mixture was heated to 80° C. for 1 more hour. After the mixture was cooled 50 ml of 5% by wt. hydrochloric acid was added, the phases separated, and the organic phase subjected to fractional distillation. 144 g of desired end product was obtained, corresponding to 80% of the theoretical amount.

Boiling point at 0.2 mbar: 62° C.

Odor: fresh-herbal, slightly minty and sweet, balsamic-woodsy like rosemary.

EXAMPLE 5

Preparation of 1-(1,4,6-trimethylcyclohex-3-en-1-yl)propan-1-ol

A solution of 0.075 moles (2.85 g) lithium aluminum hydride in 150 ml absolute diethyl ether was put in a 250-ml 3-necked flask with a magnetic stirrer, high-power condenser, dropping funnel and internal thermometer. 0.2 moles (36 g) 1-(1,4,6-trimethylcyclohex-3-en-1-yl)propan-1-one (as per Example 4) was added dropwise to this solution with cooling. Then heating with refluxing was carried out for an hour, followed by cooling, and water was added to the reaction mixture until hydrogen evolution ended. Then enough 2N hydrochloric acid was added so that the precipitate formed could be dissolved. Lastly the phases were separated, the organic phase dried with sodium sulfate and the solvent drawn off. After fractional distillation via a 30-cm Vigreux column the desired end product was obtained in practically quantitative yield.

Boiling point: 65° C. at 0.15 mbar

Odor: fresh citrus with earthy-woodsy aspects.

EXAMPLE 6

Preparation of 2-(1,4,6-trimethylcyclohex-3-en-1-yl)butan-2-ol (a) The appropriate Grignard compound was prepared from 12 g magnesium powder by the procedure according to Example 3a.

(b) Analogous to Example 3b, 0.4 moles (72 g) 1-(1,4,6-trimethylcyclohex-3-en-1-yl)propan-1-one (as per Example 4) was reacted with the Grignard compound (as per (a)). The target product was obtained in a yield of 48 g, corresponding to 62% of the theoretical amount.

Boiling point: 80° C. at 0.2 mbar

Odor: fresh spicy, slightly minty, woodsy-balsamic, brillant, patchouli and sage character.

EXAMPLE 7

Preparation of 1,4,6-trimethylcyclohex-3-ene-1-carbaldehyde

A solution of 0.2 moles (26.2 g) anhydrous aluminum chloride in 4 moles (336 g) 2-methylbut-2-en-1-al was put in a 2-liter 4-necked flask with a stirrer, high-power condenser, dropping funnel and internal thermometer. 6 moles (600 ml) isoprene were added dropwise to this solution at 40° C. Then the mixture was heated to 60° C. for another hour. After it was cooled 200 ml 5% by wt. hydrochloric acid was added, the phases separated and the organic phase subjected to fractional distillation via a 60 cm packed column. 350 g desired end product, corresponding to 58% of the theoretical amount, were obtained.

Boiling point: 75° C. at 16 mbar

Odor: fresh citrus, green, spicy-woodsy, ginger aspects.

EXAMPLE 8

Preparation of 1,4,6-trimethylcyclohex-3-ene-1-carbinol

The desired end product was obtained analogously to the procedure according to Example 5 in practically quantitative yield by reduction of 1,4,6-trimethylcyclohex-3-ene-1-carbaldehyde (as per Example 7) with lithium aluminum hydride.

Boiling point: 84° C. at 16 mbar

Odor: strongly minty-sweet, earthy

EXAMPLE 9

Preparation of 1,4,6-trimethylcyclohex-3-ene-1-carboxylic acid methyl ester (a) 0.2 moles 1,4,6-trimethylcyclohex-3-ene-1-carbaldehyde (as per Example 7) in 100 ml diethyl ether was put in a 500-ml 3-necked flask with a reflux condenser and stirrer. Chromosulfuric acid (0.07 ml sodium dichromate, 15 ml concentrated sulfuric acid, 100 ml water) was added dropwise with stirring to this solution at 25° C.

(b) 0.15 moles (11 ml) thionyl chloride was added to 0.1 moles (16.8 g) 1,4,6-trimethylcyclohex-3-ene-1-carboxylic acid (as per (a)) in a 100-ml 3-necked flask with a magnetic stirrer, reflux condenser, dropping funnel and internal thermometer and heated with refluxing for one hour. After that excess thionyl chloride was distilled off.

(c) 0.2 moles (8 ml) methanol, 0.15 moles (12 ml) pyridine and 50 ml toluene were put in a 100-ml beaker with a magnetic stirrer, and the crude product as per (b) was (1,4,6-trimethylcyclohex-3-en-1-carboxylic acid chloride) added dosewise with vigorous stirring. The reaction mixture was stirred for another hour at room temperature and then 25 ml water and 5 ml concentrated hydrochloric acid were added to it. Then the phases were separated, the organic phase dried with sodium sulfate and distilled via the Vigreux column after removal of the solvent.

The desired end product yield was 13.5 g, corresponding to 75% of the theoretical amount.

Boiling point: 91° C. at 12 mbar

Odor: sweet-herbal, minty

EXAMPLE 10

Perfume base with cologne character

| | a parts by wt. | b parts by wt. |
|---|---|---|
| Grapefruit oil | 60 | 60 |
| Orange oil, Florida | 90 | 90 |
| Cedarwood oil, Texas | 60 | 60 |
| Linalool | 100 | 100 |
| Linalyl acetate | 170 | 170 |
| Alpha-Amylcinnamic aldehyde | 90 | 90 |
| Lavender oil, Barreme | 80 | 80 |
| Clove leaf oil | 30 | 30 |
| Litsea cubeba oil | 60 | 60 |
| Elemi | 30 | 30 |
| Jasmine base 4a (10% in ethanol) | 50 | 50 |
| Nerol | 50 | 50 |
| Compound 1 | — | 130 |
| | 870 | 1000 |

Composition a displays a fresh fruity odor with marked citrus nuances. Somewhat unexpectedly and without a proper blending or obvious link, herbal aspects are recognizable in addition. The fruity and herbal-woodsy components are blended by the addition of 13% 1-(1,4,6-trimethylcyclohex-3-en-1-yl)ethan-1-one (composition b) to produce a harmonious fragrance picture of a spicy-masculine cologne.

EXAMPLE 11

Floral chypre base

| | a parts by wt. | b parts by wt. |
|---|---|---|
| Bergamot oil, Reggio | 150 | 150 |
| Oakmoss, Res. Luxol | 50 | 50 |
| alpha-Isomethylionene | 150 | 150 |
| Geranium oil, Bourbon | 30 | 30 |
| Jasmine base 4a (10% in ethanol) | 50 | 50 |
| Vetiveryl acetate | 60 | 60 |
| clove bud oil | 50 | 50 |
| Ylang-ylang oil | 50 | 50 |
| Amyl salicylate | 60 | 60 |
| Benzyl acetate | 70 | 70 |
| Linalyl acetate | 100 | 100 |
| Musk ketone | 50 | 50 |
| Labdanum resinoid | 30 | 30 |
| Undecalactone (10% in ethanol) | 50 | 50 |
| Compound 3 | — | 50 |
| | 950 | 1000 |

The addition of 5% 2-(1,4,6-trimethylcyclohex-3-en-1-yl)propan-2-ol to the classic chypre theme a causes a powerful increase in brilliance and elegance. Despite the accentuation of the oakmoss and woodsy aspects, the composition as a whole seems to be more balanced and mellower.

EXAMPLE 12

Woodsy base

| | a parts by wt. | b parts by wt. |
|---|---|---|
| Bergamot oil, Reggio | 120 | 120 |
| Linalyl acetate | 140 | 140 |
| Sandalwood oil, East Indian | 120 | 120 |
| p-tert.-Butylcyclohexyl acetate | 100 | 100 |
| Cedryl acetate | 120 | 120 |
| Jasmine base 4a, 10% in ethanol | 100 | 100 |
| Methylionene | 80 | 80 |
| Patchouli oil | 100 | 100 |
| Compound 3 | — | 120 |
| | 880 | 1000 |

If 12% 2-(1,4,6-trimethylcyclohex-3-en-1-yl)propan-2-ol is added to the woodsy composition the brilliance is increased enormously. The fragrance picture of fine woods is intensified. Moreover the new ingredient has a fixative action and imparts a warm, powdery back note to the base.

While only several embodiments and examples of the present invention have been described, it is obvious that many changes and modifications may be made thereunto without departing from the spirit and scope of the invention.

What is claimed is:

1. 1-(1,4,6-trimethylcyclohex-3-en-1-yl)-ethan-1-ol.
2. 1-(1,4,6-trimethylcyclohex-3-en-1-yl)-propan-1-one.
3. (1,4,6-trimethylcyclohex-3-en-1-yl)methanol.
4. 1-(1,4,6-trimethylcyclohex-3-en-1-yl)-1-methylethan-1-ol.
5. 1-(1,4,6-trimethylcyclohex-3-en-1-yl)-1-methylpropan-1-ol.

* * * * *